US012704499B2

(12) United States Patent
Toreyin

(10) Patent No.: US 12,704,499 B2
(45) Date of Patent: Aug. 11, 2026

(54) HIGH SPATIAL RESOLUTION CELLULAR MONITORING TECHNOLOGY SYSTEMS AND METHODS

(71) Applicant: San Diego State University (SDSU) Foundation, San Diego, CA (US)

(72) Inventor: Hakan Toreyin, San Diego, CA (US)

(73) Assignee: San Diego State University (SDSU) Foundation, San Diego, CA (US)

( * ) Notice: Subject to any disclaimer, the term of this patent is extended or adjusted under 35 U.S.C. 154(b) by 1192 days.

(21) Appl. No.: 17/128,224

(22) Filed: Dec. 21, 2020

(65) Prior Publication Data

US 2021/0247375 A1 Aug. 12, 2021

Related U.S. Application Data

(60) Provisional application No. 62/952,062, filed on Dec. 20, 2019.

(51) Int. Cl.
*G01N 33/483* (2006.01)

(52) U.S. Cl.
CPC ..... *G01N 33/4836* (2013.01); *G06F 2218/04* (2023.01); *G06F 2218/08* (2023.01); *G06F 2218/16* (2023.01); *G06F 2218/22* (2023.01)

(58) Field of Classification Search
CPC ............ G06F 2218/22; G06F 2218/16; G06F 2218/12; G06F 2218/18; G06F 2218/10; G06F 3/015; G08B 21/0453
See application file for complete search history.

(56) References Cited

U.S. PATENT DOCUMENTS

2016/0242690 A1* 8/2016 Principe ................. A61B 5/316

OTHER PUBLICATIONS

Christophe Pouzat, Ofer Mazor, Gilles Laurent, Using noise signature to optimize spike-sorting and to assess neuronal classification quality, Journal of Neuroscience Methods, vol. 122, Issue 1, 2002, pp. 43-57, ISSN 0165-0270, https://doi.org/10.1016/S0165-0270(02)00276-5. (Year: 2002).*
Castellanos, A. P. (2018). Stochastic Resonance in Neural Network, Noise Color Effects. arXiv preprint arXiv:1810.06731 (Year: 2018).*
Sunghan Kim, James McNames, Automatic spike detection based on adaptive template matching for extracellular neural recordings , Journal of Neuroscience Methods, vol. 165, Issue 2, 2007, pp. 165-174, ISSN 0165-0270 (Year: 2007).*
B. Ando and S. Graziani, "Adding noise to improve measurement," in IEEE Instrumentation & Measurement Magazine, vol. 4, No. 1, pp. 24-31, Mar. 2001, doi: 10.1109/5289.911170. (Year: 2001).*
Thomas Wellens et al 2004 Rep. Prog. Phys. 67 45 (Year: 2004).*
Hong G, Lieber CM. Novel electrode technologies for neural recordings. Nat Rev Neurosci. Jun. 2019;20(6):330-345. doi: 10.1038/s41583-019-0140-6. (Year: 2019).*

* cited by examiner

*Primary Examiner* — Catherine T. Rastovski
*Assistant Examiner* — Brian Butler Geiss
(74) *Attorney, Agent, or Firm* — Jared Aizad; Buchalter

(57) ABSTRACT

A system and method for detecting, amplifying, and sorting non-transitory signals stemming from cellular activity of tissue in an extracellular medium is presented herein. Weak signals are difficult to detect, especially when they originate far from the measuring electrode. The invention takes advantage of stochastic resonance, i.e. adding noise to signals to amplify them and make them more detectable, to improve signal detection from a single electrode.

19 Claims, 14 Drawing Sheets

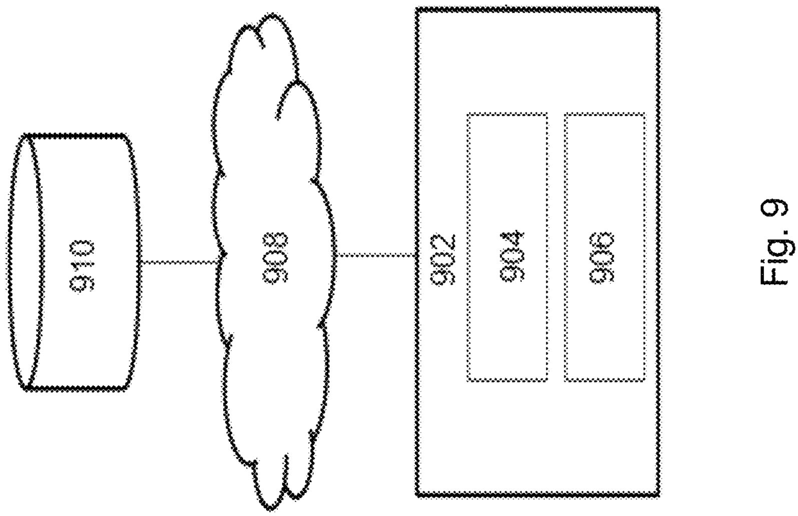
Fig. 9

HIGH SPATIAL RESOLUTION CELLULAR MONITORING TECHNOLOGY SYSTEMS AND METHODS

CROSS-REFERENCE TO RELATED APPLICATIONS

This application claims priority from U.S. Provisional Application No. 62/952,062 filed on Dec. 20, 2019, which is incorporated herein by reference in its entirety.

STATEMENT REGARDING FEDERALLY SPONSORED RESEARCH OR DEVELOPMENT

This invention was made with government support under award no. 1916160 awarded by the U.S. National Science Foundation. The government has certain rights in the invention.

FIELD

The present disclosure generally relates to systems and methods for detecting, amplifying, and sorting cellular activity in a tissue in an extracellular medium.

BACKGROUND

The state of the art extracellular recording and computation systems suffer from a small number of observable cells per electrode and low scalability. It is typical for the number of cells to be undercounted. While tissue damage by the electrode is one cause for the discrepancy, another cause is that the amplitude of signals far from the electrode is often too weak to be detected and are below the background noise level of the extracellular medium.

Stochastic resonance is a phenomenon by which noise is added to a weak signal so that it is detectable. There are no systems that use stochastic resonance to detect, amplify, and sort signals. Such a system would be invaluable for high spatial resolution extracellular monitoring.

SUMMARY

The present teachings include methods for processing non-transitory signals generated by cellular activity in a tissue, with the steps comprising placing an electrode, optode, or other form of a detector, in an extracellular media with tissue, recording cellular activity generated by the electrode, filtering the recorded activity into signals of varying intensity via an algorithm, generating an index array comprising indices of data points exceeding a threshold and grouping successive indices into a single value to create a time array of detected signals, wherein the time array corresponds to enhanced detection, amplification, and sorting of the cellular activity in the tissue. The signal may exist in a number of forms. In an embodiment, the signal may be electrical. In another embodiment, the signal may be optical. In another embodiment, the signal may be sound. In another embodiment, the signal may be electromagnetic. In another embodiment, the signal may be magnetic. In effect, the signal may be any detectable and appropriate signal.

In accordance with a further aspect, the cellular tissue that generates the signal may be from a variety of sources, including, but not limited to, neuronal tissue, cardiac tissue, lung tissue, muscle tissue, bone tissue, and other tissues that are derived from life forms.

In accordance with yet a further aspect, noise that is added to signals amplifies them so that they are detectable.

In accordance with yet a further aspect, filtering of the signals is achieved with a finite-element-response (FIR) filter.

In accordance with yet a further aspect, in an embodiment white noise is added to the signal to increase the signal's detection. In another embodiment, flicker noise is added to the signal to increase the signal's detection. In yet another embodiment, a combination of white noise and flicker noise is added to the signal to increase the signal's detection.

In accordance with yet a further aspect, the signal generated by cellular activity may be measurable about 140 microns away from the electrode. This is significant, since as the distance from the electrode increases, the detectability of the signal decreases. In another embodiment, cellular activity may be measurable more than 140 microns from the electrode. The strength of the signal is a variable that determines the signal's detectability.

In accordance with yet a further aspect, the method that detects, amplifies, and sorts signals is executable through a variety of programs. In an embodiment, MATLAB may be the program. In another embodiment, GNU Octave is the program. In yet another embodiment, SciLAB is the program. In any event, any program that is capable of detecting, amplifying, and sorting signals may be used.

In accordance with yet a further aspect, flicker noise that is added to a signal may vary in frequency.

In accordance with yet a further aspect, the ratio of the standard deviation of flicker or white noise and the standard deviation of background noise varies. This is significant, because, depending on the threshold, increasing the ratio may increase the detectability of the signal.

In accordance with yet a further aspect, signal performance is measurable by sensitivity, a performance metric that is also known as true positive rate.

In accordance with yet a further aspect, a threshold is applied to signals after noise is weighed and added to the signals.

In accordance with yet a further aspect, the threshold that is applied to the signals is variable. This is significant since sensitivity may be affected by increasing threshold.

In accordance with yet a further aspect, signals of similar amplitude are grouped together, sorting amplitudes.

In accordance with yet a further aspect, the activity of the signals dictates sorting. High activity signals are separated from silent and medium activity signals.

In accordance with yet a further aspect, the FIR filter used for filtering signals varies in frequency. In an embodiment, a range from 300 Hz to 3 kHz is allowable. In another embodiment, a range from 300 Hz to 6 KHz is allowable. In other embodiments, other frequency ranges may also be permissible.

In accordance with yet a further aspect, the value of the threshold applied to the signals is a multiple of the standard deviation of background noise and is variable. This is significant, as threshold may affect sensitivity based on an increasing standard deviation of background noise.

In accordance with yet a further aspect, in an embodiment, the multiple of the standard deviation of background noise ranges between 3 and 5. In other embodiments, other ranges are permissible.

In accordance with yet a further aspect, in an embodiment, the ratio of the standard deviation of flicker noise and the standard deviation of background noise ranges between 0 and 75. Other embodiments may allow for other ranges.

In accordance with yet a further aspect, time array values within 500 microseconds of the closest index array is considered a true positive, or detectable.

The present teachings also include a computer program comprising non-transitory computer executable code in a non-transitory computer readable medium that, when executing on one or more computing devices (e.g. laptop, tablet computer, desktop, or any other device that handles computer code), performs the steps of: placing an electrode in an extracellular medium containing tissue, recording cellular activity generated by the electrode, filtering the recorded activity into signals of varying intensity via an algorithm, generating an index array comprising indices of data points exceeding a threshold and grouping successive indices into a single value to create a time array of detected signals. The time array corresponds to enhanced detection, amplification, and sorting of the cellular activity in the tissue.

The present teachings also include a system comprising: a computing device including a network interface for communications over a data network for amplification and sorting of cellular activity in a tissue comprising: a signal amplification and sorting engine having a processor and a memory, the signal amplification and sorting engine including a network interface for communications over the data network, the signal amplification and sorting engine configured to initiate an algorithm that filters signals from recorded cellular activity into signals of varying intensity, generates an index array comprising indices of data points exceeding a threshold, and groups successive indices into a single value to create a time array of detected signals, wherein the time array corresponds to enhanced detection, amplification, and sorting of the cellular activity in the tissue.

The present teachings also include a computer-implemented method comprising: placing an electrode in an extracellular medium with tissue, recording cellular activity of the tissue generated by the electrode, filtering the recorded activity into signals of varying intensity via an algorithm, generating an index array comprising indices of data points exceeding a threshold, and grouping successive indices into a single value to create a time array of detected signals. The time array corresponds to enhanced detection and sorting of the cellular activity in the tissue.

These and other features, aspects and advantages of the present teachings will become better understood with reference to the following description, examples, and appended claims.

BRIEF DESCRIPTION OF THE DRAWINGS

The foregoing and other objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein

FIGS. 3A-C all show a threshold level (red line), detected signal times (red dots), and ground truth signal times (black dots) for each signal.

FIG. 9 is a computing environment for evaluating the detection, amplification and sorting of the signals.

DETAILED DESCRIPTION

Figure 1:
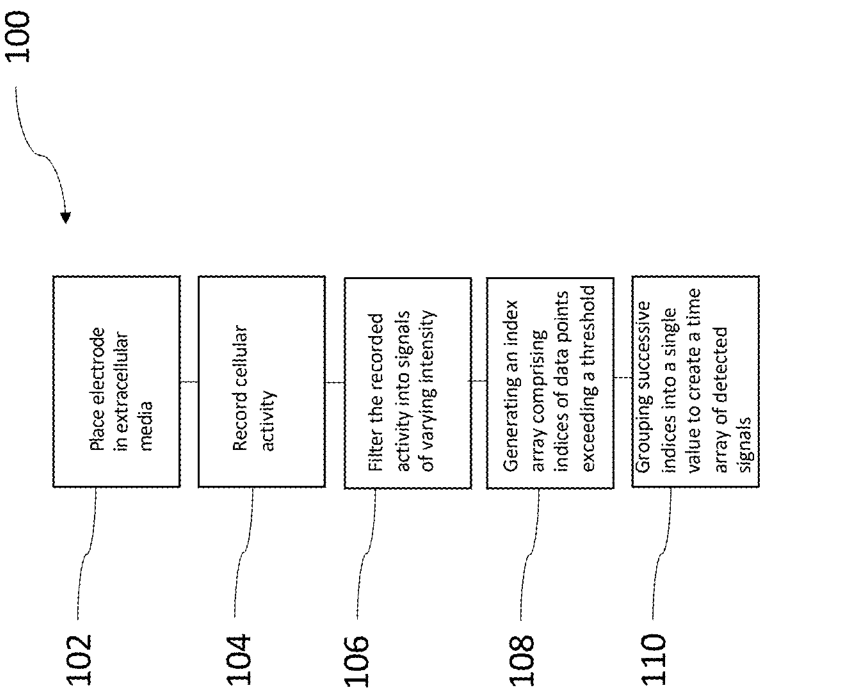
FIG. 1 is a flow chart of a method for detecting, amplifying and sorting signals from cellular activity.

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term “or” should generally be understood to mean “and/or” and so forth.

Recitation of ranges of values herein are not intended to be limiting, referring instead individually to any and all values falling within the range, unless otherwise indicated herein, and each separate value within such a range is incorporated into the specification as if it were individually recited herein. The words “about,” “approximately,” or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language (“e.g.,” “such as,” or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as “first,” “second,” “top,” “bottom,” “up,” “down,” and the like, are words of convenience and are not to be construed as limiting terms.

In general, described herein are devices, systems, and methods for detection, amplification and sorting of signals. As used throughout this disclosure, “detection” of signals may include uncovering, to a particular degree or range of certainty (which may be a predetermined degree/range, or a degree/range following standard industry practice), signals in a sample of tissue within an extracellular medium. Thus, detection may include discovering, affirming, finding, uncovering, unearthing, revealing, exposing, etc., signals in a sample. The tissue may be of any cellular kind. As used throughout this disclosure, “amplification” of signals may include may include increasing, making more detectable, or making larger, the signal.

Although devices, systems, and methods discussed herein generally describe the detection, amplification, and sorting of signals stemming from cellular activity of a tissue within an extracellular neural medium, detection, amplification and sorting of any signal may also or instead be enabled by the devices, systems, and methods discussed herein. For example, devices, systems, and methods discussed herein can be adapted to detect, amplify and sort soundwave signals, electrical signals, optical signals, and so forth. Also, although cellular activity may include activity from any type of cells. The devices, systems, and methods discussed herein can be adapted to detect, amplify, and sort signals from, without limitation, neurons, cardiac cells, lung cells, muscle cells, bone cells, glial cells, and so forth. Furthermore, embodiments generally described herein are detecting, amplifying and sorting signals stemming from cellular activity from human beings, animals, and other forms of life.

FIG. 1 is a flow chart of a method for detecting, amplifying and sorting signals from cellular activity. In general, the method 100 may involve processing and analyzing signals stemming from cellular activity of a tissue in an extracellular media. The goal of the processing and analyzing is to detect previously undetectable weak signals, amplify those signals, and sort signals based on the cells they originate from.

As shown in step 102, the method 100 may include placing an electrode in an extracellular media with tissue made up of cells or cellular matter. The cells may be derived from any life form, and generate a signal sensed by the electrode. Based on the placement of the electrode, the cells will emit a weaker or stronger signal. The amplitude of signals located at distances greater than 140 micrometers (μm) typically stay below the background noise level of the extracellular medium and are difficult to detect.

As shown in step 104, the method 100 may include recording the signal by the cells in the extracellular media. In an example, neurons in extracellular media may generate an imbalanced dataset, where the number of signals corresponding to the low-baseline neurons are significantly smaller than those of medium- or high-baseline activity neurons. In another example, a synthetic dataset may consist of two 250 s recordings with a sampling rate of 20 kHz. Signals from a neuron is weighed based on the neuron’s distance from the electrode, r through $e^{-r/r0}$, where $r_0$ is taken as 28 μm following values reported in the literature based on measurements As shown in step 106, the method 100 may include filtering the signals into signals of varying intensity. In an example, the algorithm that is initiated by filtering implements bandpass filtering ranging from 300 Hz-3 kHz using a finite-impulse-response (FIR) filter. The algorithm also acts by adding noise to the signals to make weaker signals more detectable. The phenomenon, stochastic resonance, works by enhancing weak signal detection in nonlinear threshold-based detection systems by adding an optimal level of noise to the signal. Noise is then added to the filtered signals. The noise can be, but is not limited to, white noise and flicker noise. In an example, flicker noise signal is weighed and added to the filtered signal. In this example, the added flicker noise weights are selected such that the ratio of the standard deviation of the flicker noise ($\sigma_{1/f}$) and the standard deviation of the background noise ($\sigma_{bg}$) varies between 0-20.

As shown in step 108, the method 100 may include generating an index array comprising indices of data points exceeding a threshold. In an example, the threshold is selected automatically based on the standard deviation of the background noise ($\sigma_{bg}$), and is a multiple of $\sigma_{bg}$. In this example, the multiple has values between 3 and 5.

As shown in step 110, the method 100 may include grouping successive indices into a single value to create a time array of detected signals. In an example, detected signal time array values that are within 500 μs window of the nearest signal in the ground truth index array is considered as true positive, with sensitivity (true positive rate) being the signal detection performance assessment metric.

Figure 2:
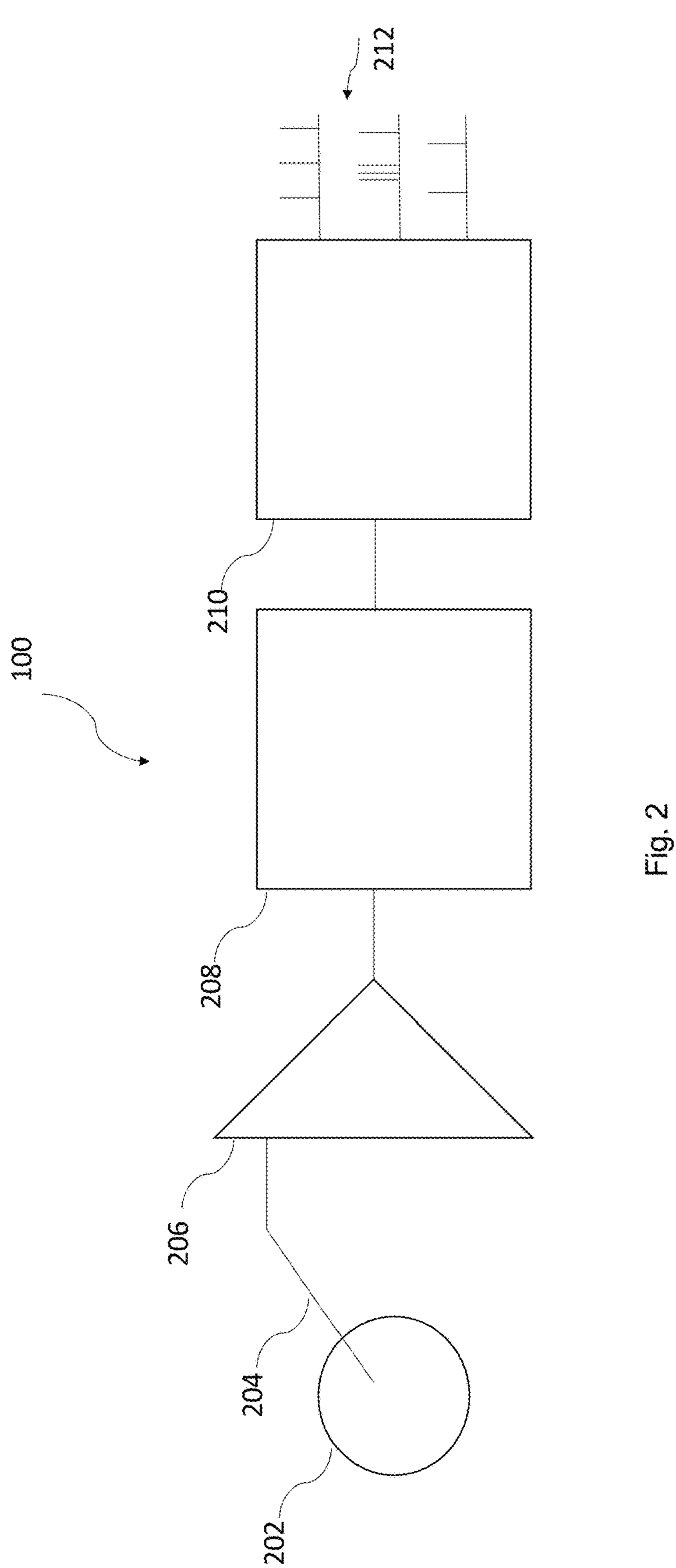
FIG. 2 depicts a spike recording and sorting system.

FIG. 2 is an alternative depiction of the method 100. The electrode 204 placed in the extracellular medium 202 is connected to a recorder 206. A signal detection step 208 filters the signals and adds noise to the signals measuring against a threshold to amplify the signals. A signal sorting step 210 groups the successive values of the index array into a single value to create a time array of detected signals, the final output of which is sorted signals 212.

Figures 3A, 3B, 3C:
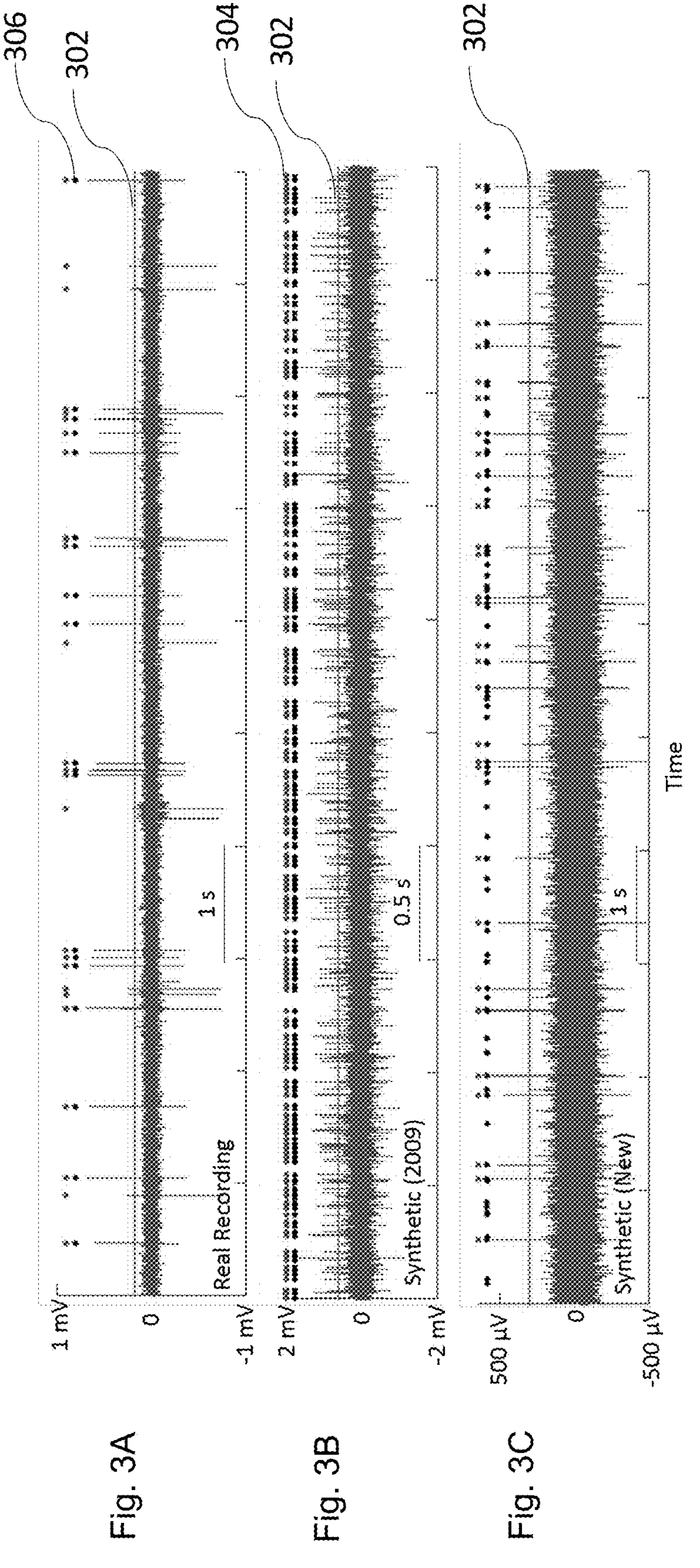
FIGS. 3A-C shows signal recordings from the hippocampus region of rats (A), synthetic signals (B), and another set of synthetic signals (C).

FIGS. 3A-C depicts plots of signals from three different datasets. FIG. 3A shows recordings from hippocampus region of rats, FIG. 3B shows synthetic signals taken from the literature, and FIG. 3C shows synthetic signals of neurons located in three different distances from the recording electrode. A threshold line 302, shown in FIG. 3A, FIG. 3B, and FIG. 3C, demarcates detected from undetected signals. A detected signal 304, as shown in FIG. 3B, is shown as a red dot, while ground truth signals 306, as shown in FIG. 3A, are shown as black dots. The ground truth signals 306 are obtained by simultaneous intracellular recordings.

Figures 4A, 4B, 4C:
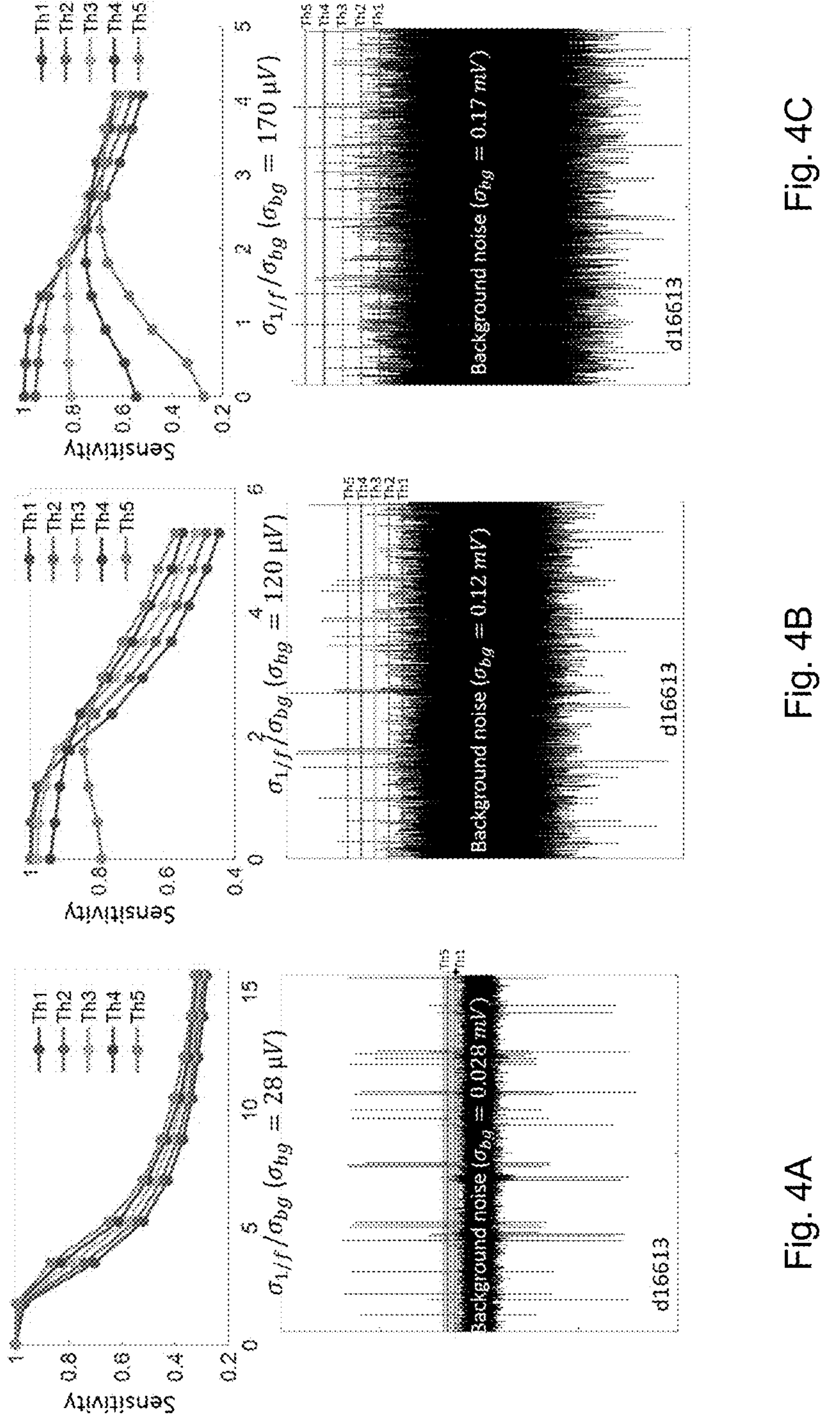
FIGS. 4A-C depict signal detection sensitivity versus flicker noise (1/f) intensity for a cellular recording at five different threshold levels.

FIG. 4 depicts sensitivity changes as flicker noise is added to the signals. FIG. 4A shows that, with lower background noise, adding noise (x-axis) degrades the sensitivity (the y-axis). As background noise increases, as seen in FIGS. 4B and 4C, adding flicker noise improves sensitivity at higher thresholds. In FIG. 4B, a threshold of 600 microvolts (5*120 microvolts), shown as Th5, produces a bell curve whereby sensitivity increases with adding flicker noise before dropping. FIG. 4C, at thresholds of 680 microvolts (Th3), 765 microvolts (Th4), and 850 microvolts (Th5), a bell curve is also apparent, increasing with adding flicker noise before dropping.

Figures 5A, 5B, 5C:
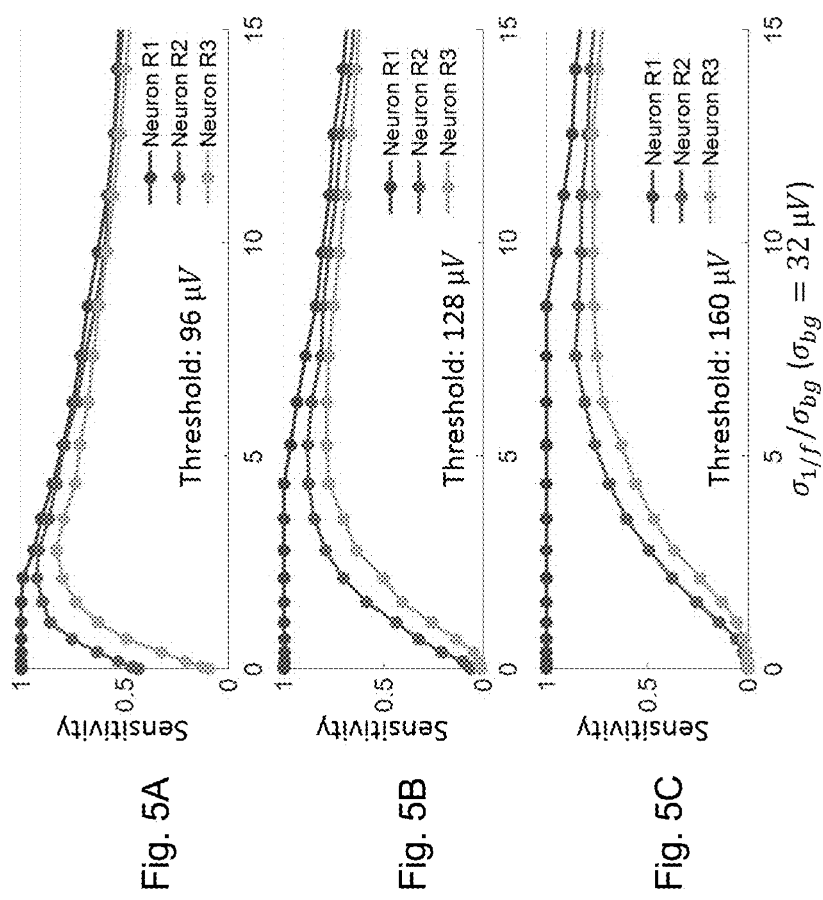
FIGS. 5A-C illustrate signal detection sensitivity of three regions of cells at three different thresholds.

FIGS. 5A, 5B, and 5C show another illustration of increasing sensitivity (y axis) with adding flicker noise (x axis). The signals of neurons at 3 different distances from the electrode and at 3 different thresholds at a constant background noise (32 microvolts) are measured, with R1 being closer to the electrode than R2, and R2 being closer to the electrode than R3. With adding flicker noise and as threshold increased, sensitivity of the neurons in Regions 2 (R2) and 3 (R3) increases until dropping is observed. Also, as threshold increased, the sensitivity is greatest at a higher flicker noise.

Figure 6:
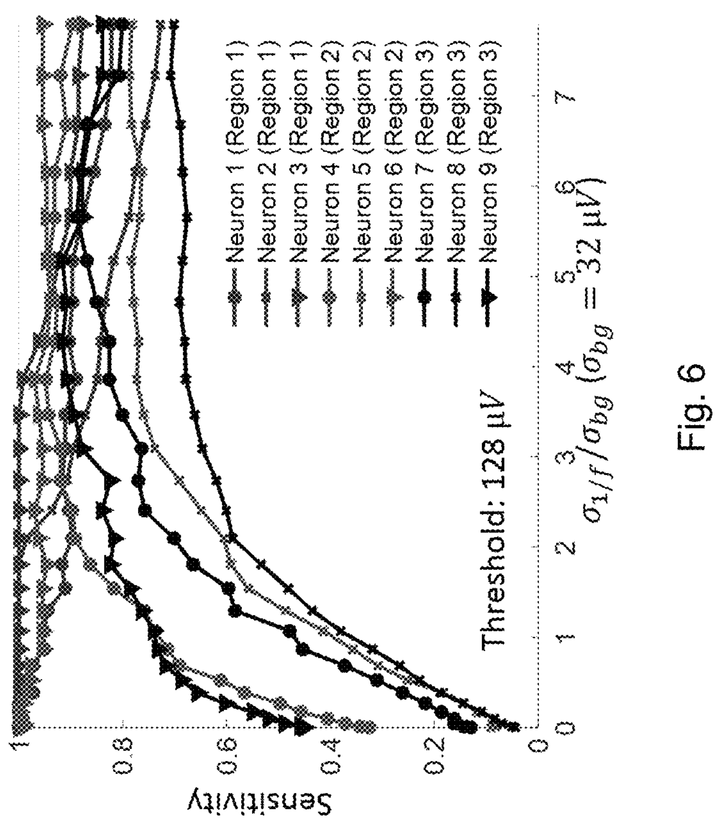
FIG. 6 depicts signal detection sensitivity of nine cells, three cells in each of the three regions, with respect to additive flicker (1/f) noise intensity.

FIG. 6 is another depiction of the effect of flicker noise on sensitivity, with 3 neurons per region and 3 regions. The sensitivity of region 1 signals decreases with additive flicker noise, whereas most of the neurons in regions 2 and 3 (namely neurons 4, 7, 8, and 9) shows sensitivity increasing with flicker noise, then a drop.

Figures 7A, 7B, 7C, 7D:
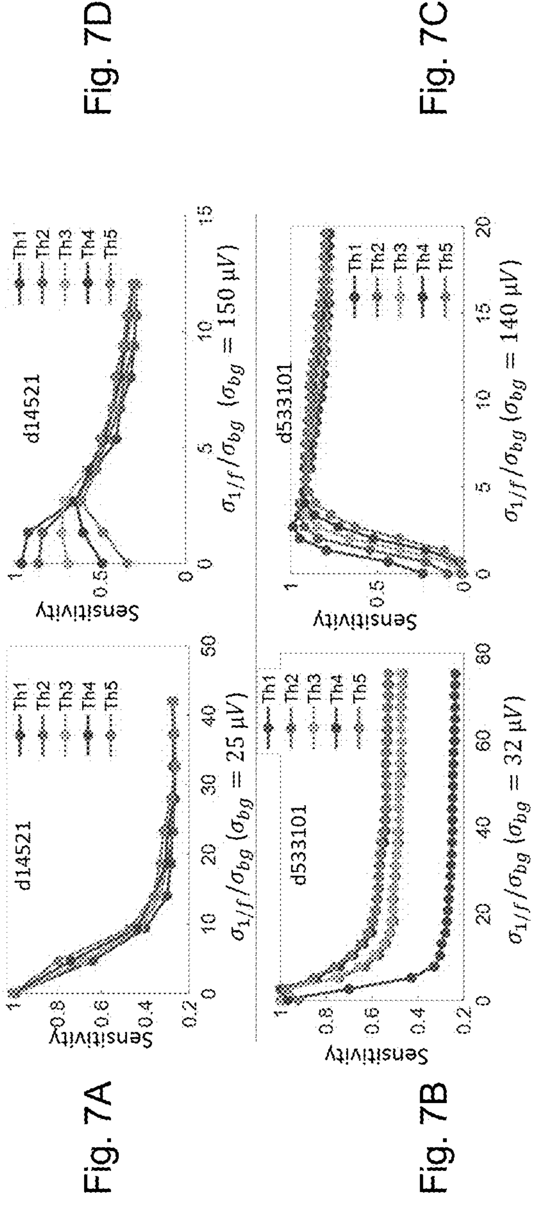
FIGS. 7A-D show signal detection sensitivities at 5 different thresholds with varying standard deviation of background noise.

FIGS. 7A, B, C, and D show yet another illustration of flicker noise's effect on sensitivity. Background noise increases from FIG. 7A to FIG. 7D. With increasing background noise, adding flicker noise increases sensitivity followed by a drop.

Figures 8A, 8B, 8C, 8D:
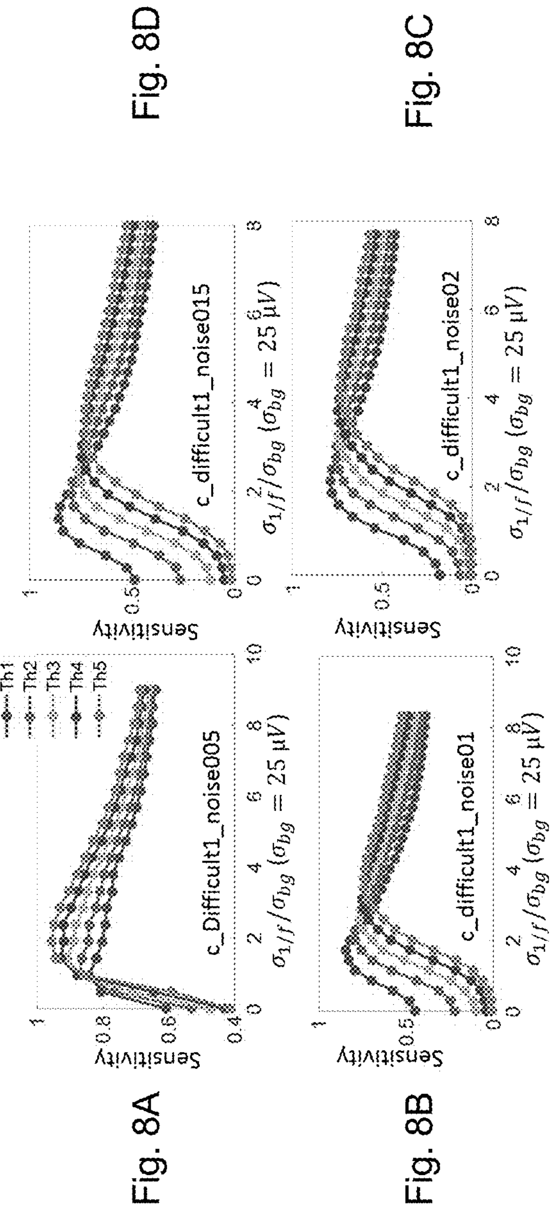
FIGS. 8A-D illustrate signal detection sensitivities at a standard deviation of background noise of 25 μV at 5 different thresholds.

FIGS. 8A, B, C and D shows yet another illustration of sensitivity and how it is affected by flicker noise, with 4 different synthetic datasets taken from the literature. As background noise stays constant, with increasing flicker noise, sensitivity increased before dropping.

FIG. 9 depicts a computing environment 900 for evaluating the detection, amplification and sorting of the signals. Device 902 can include: user interface (UI) 904 (e.g., a monitor or touch screen of a mobile device or computer) and program 906. A network 908 can connect program 906 to a database 910 via internet connection or any telecommunication. The database 910 stores information sensed by the electrode that is in contact with tissue in the extracellular medium of FIG. 2 and measured by the recorder of FIG. 2. In addition, a custom integrated-circuit solution for computing (i.e. for detection and classification of signals), such as an integrated electronics chip, may serve as the program 906.

In all the illustrations of sensitivity versus flicker noise, it is apparent that there is an optimal flicker noise amount by which signal sensitivity, and thus signal detectability, is best.

With respect to the background noise and threshold values, they are not all encompassing. While experimentation showed an observable effect of adding flicker noise on signal sensitivity with the particular values presented, other values would produce the same effect. produce the same effect.

Figures 10A, 10B, 10C:
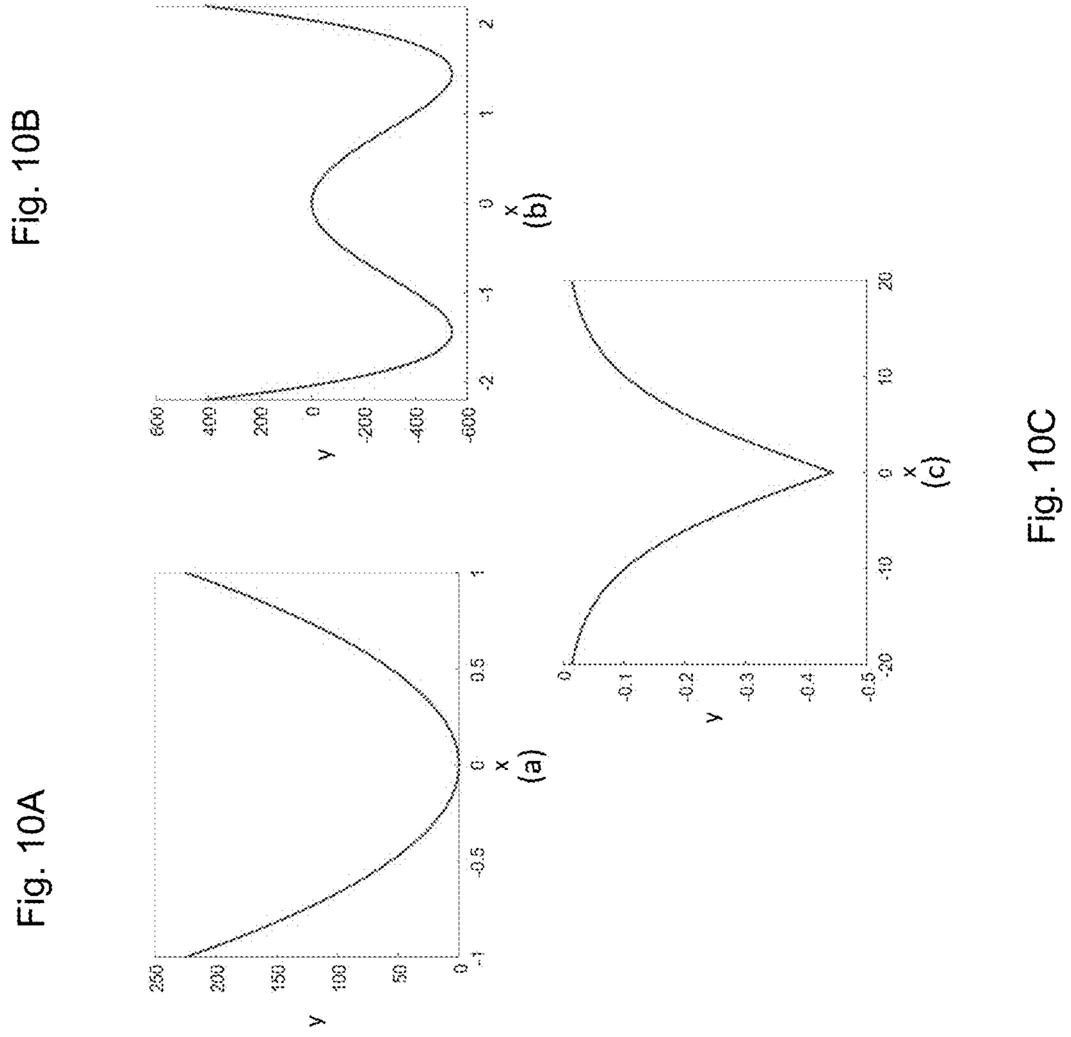
FIGS. 10A-C shows different wells that depict the movement of a Brownian particle.

FIG. 10 depicts different wells in which the movement of a Brownian particle is examined when the particle is perturbed by the noisy signal having weak extracellular spikes. A monostable (FIG. 10*a*), bistable (FIG. 10*b*), and a Wood-Saxon potential (FIG. 10*c*) are shown. The movement of the particle is governed by the by the special form of the Langevin equation with neglected inertia:

$$\frac{dx(t)}{dt} = -\frac{dU_0(x,t)}{dx} + s_n(t), \quad (1)$$

In equation 1, dx(t)/dt is the particle velocity, tracking the x-position of the particle, $U_0(x,t)$ is a potential well that the particle interacts with, and $s_n(t)=s(t)+n(t)$ is a band-pass filtered (BPF) version of the input signal with s(t) and n(t) being the signal and noise, respectively. The velocity of the particle is controlled by two terms on the right-hand side of equation 1. $-dU_o(x,t)/dx$ represents the contribution of the potential well on the particle velocity. The second term, $s_n(t)$, represents the contribution of the system input on the particle velocity. In an embodiment, a Kaiser window, a finite impulse response (FIR) filter with cut-offs 300 Hz-6 kHz, is used. used.

Inclusion of inertia in the Langevin equation leads to $$\frac{d^2x(t)}{dt^2} + \gamma\frac{dx(t)}{dt} = -\frac{dU_0(x,t)}{dx} + s_n(t). \quad (2)$$

In equation 2, $\gamma$ is the damping factor.

Figures 11A, 11B, 11C, 11D, 11E, 11F:
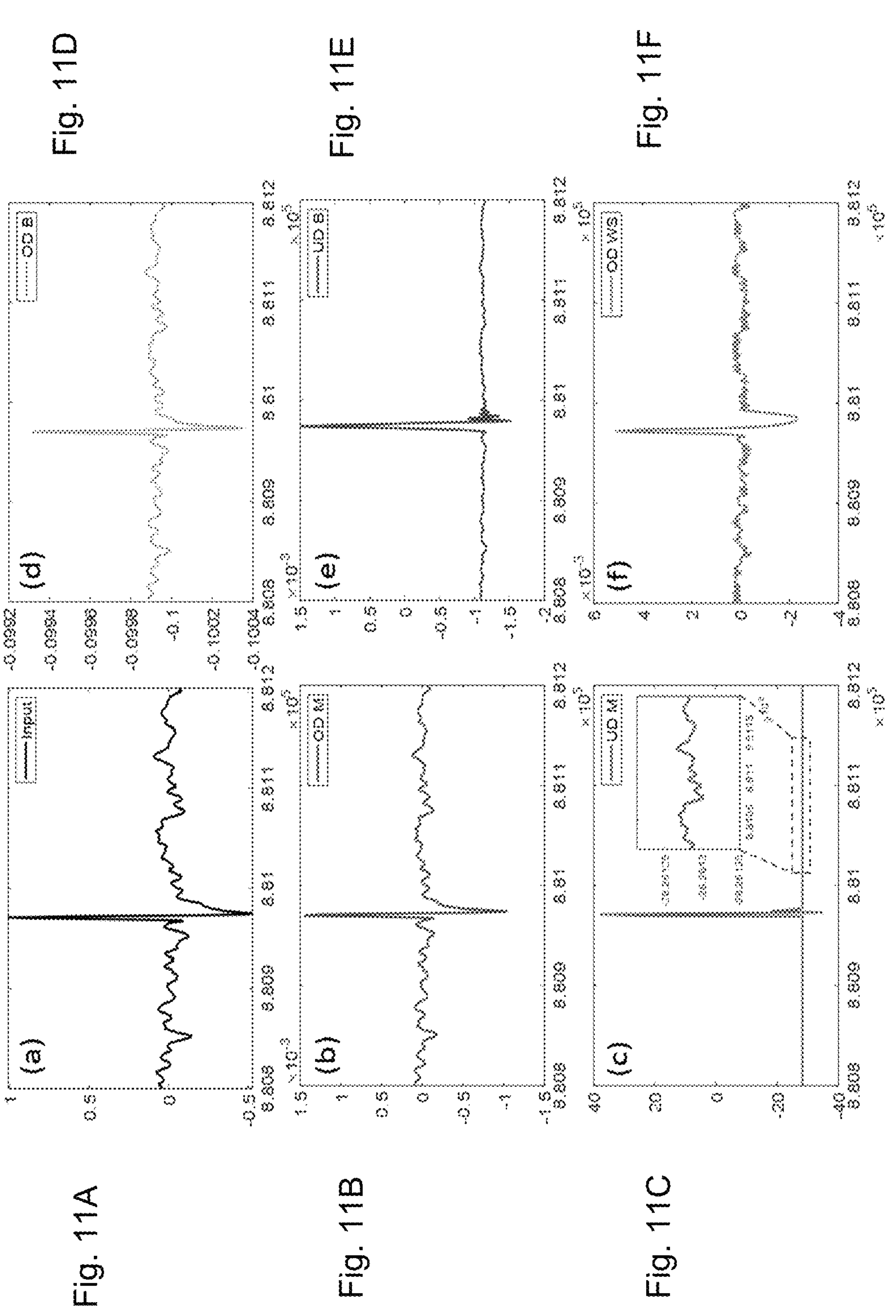
FIGS. 11A-F are signal to noise ratio (SNR) improvements of an input spike in different wells.

FIG. 11 depicts improvements in signal to noise ratio (SNR) of an input spike (FIG. 11*a*) in different wells. In addition to stochastic resonance being executed in an over-damped monostable well (OD M), as seen in FIG. 11*b*, underdamped and bistable configurations are also possible for study. FIGS. 11 *c-e* show underdamped and monostable (UD M), overdamped and bistable (OD B), and under-damped and bistable (UD B), respectively. FIG. 11*f* shows an overdamped Wood-Saxon (OD WS) potential.

SNR improvement in the UD M configuration (FIG. 11*c*) is significantly greater than in the other configurations. In an embodiment, the SNR improvement is six orders of magnitude greater in the UD M configuration than in the other configurations. In an embodiment, the significant SNR improvements with UD M may enhance electrocardiogram (ECG) measurements. In another embodiment, the SNR improvements with UD M enhances electromyography (EMG) measurements. In yet another embodiment, SNR improvements with UD M enhances electroencephalography (EEG) measurements. Other embodiments may allow for the SNR improvement in the UD M configuration to be even greater than six orders of magnitude greater than the other configurations.

Figure 12:
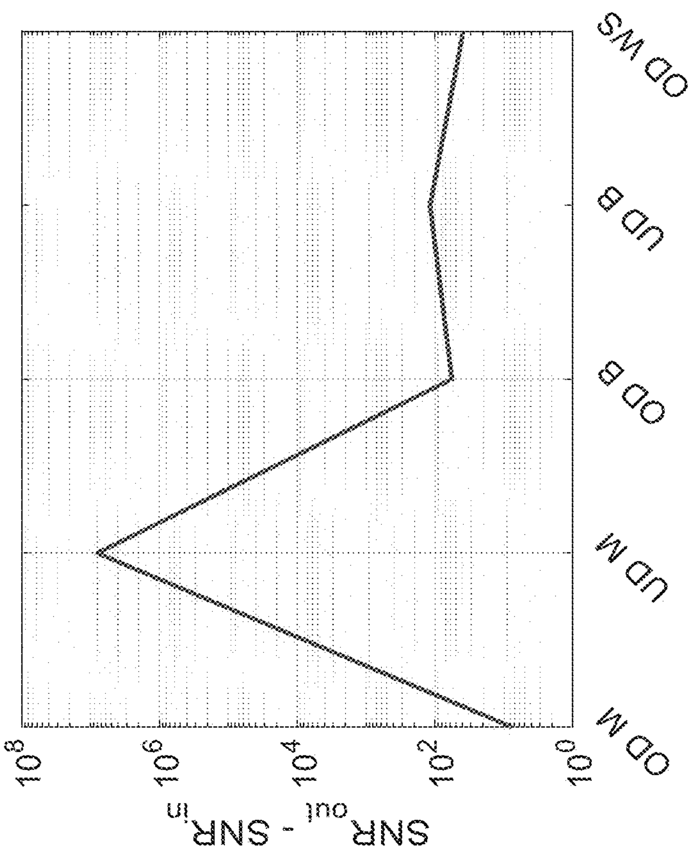
FIG. 12 depicts SNR improvement in logarithmic scale for each of different well shape and system configurations.

FIG. 12 depicts the various well configurations on a logarithmic scale, further showing that the UD M configuration is significantly greater in SNR than the other configurations.

Figure 13:
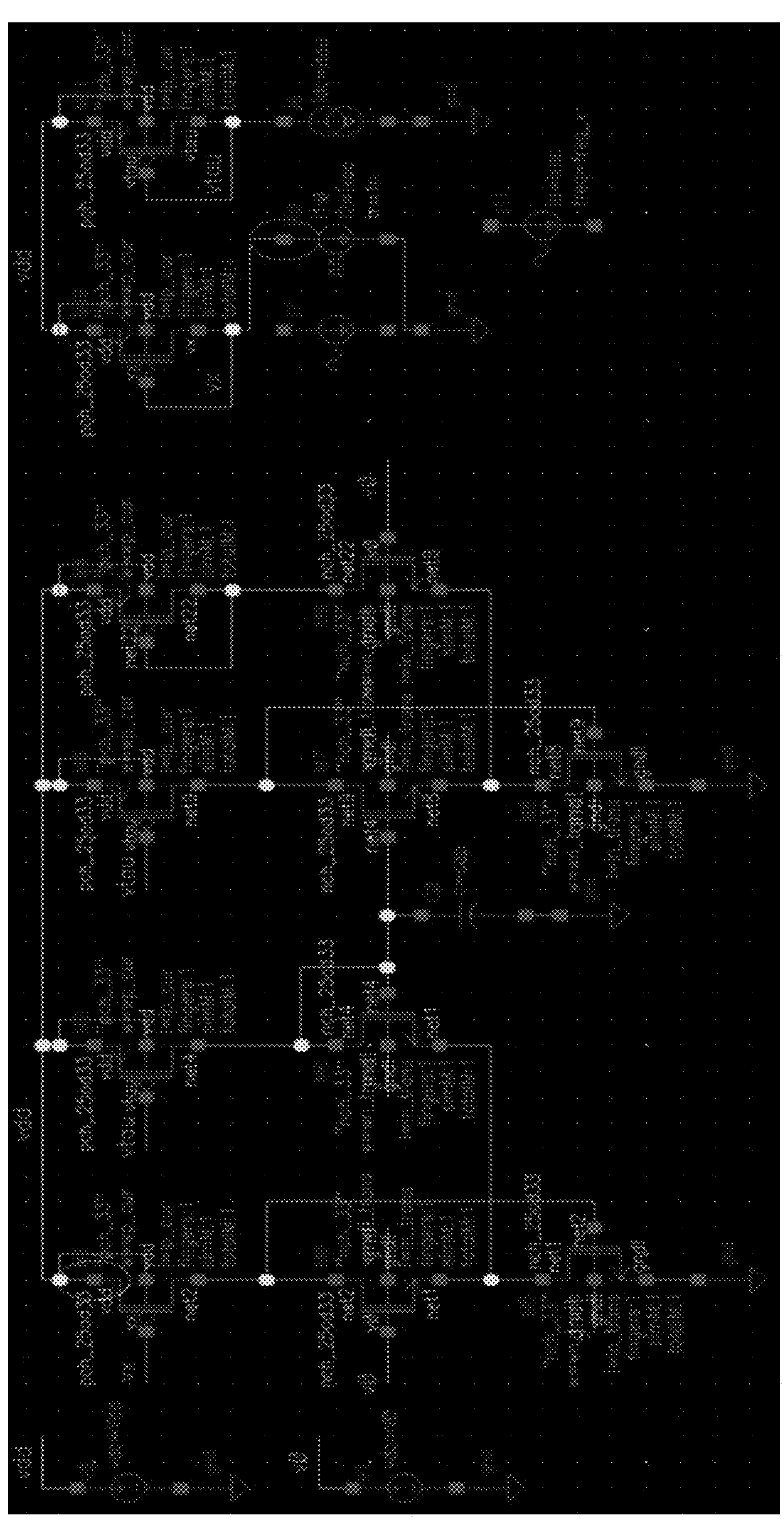
FIG. 13 is a physical implementation of a solver as an analog integrated circuit.

FIG. 13 depicts a physical implementation of a solver as an analog integrated circuit, with the solver solving the equation $$dx(t)/dt=-[ax(t)+bx^3(t)]+s_{n,F}(t) \quad (3)$$

Figure 14:
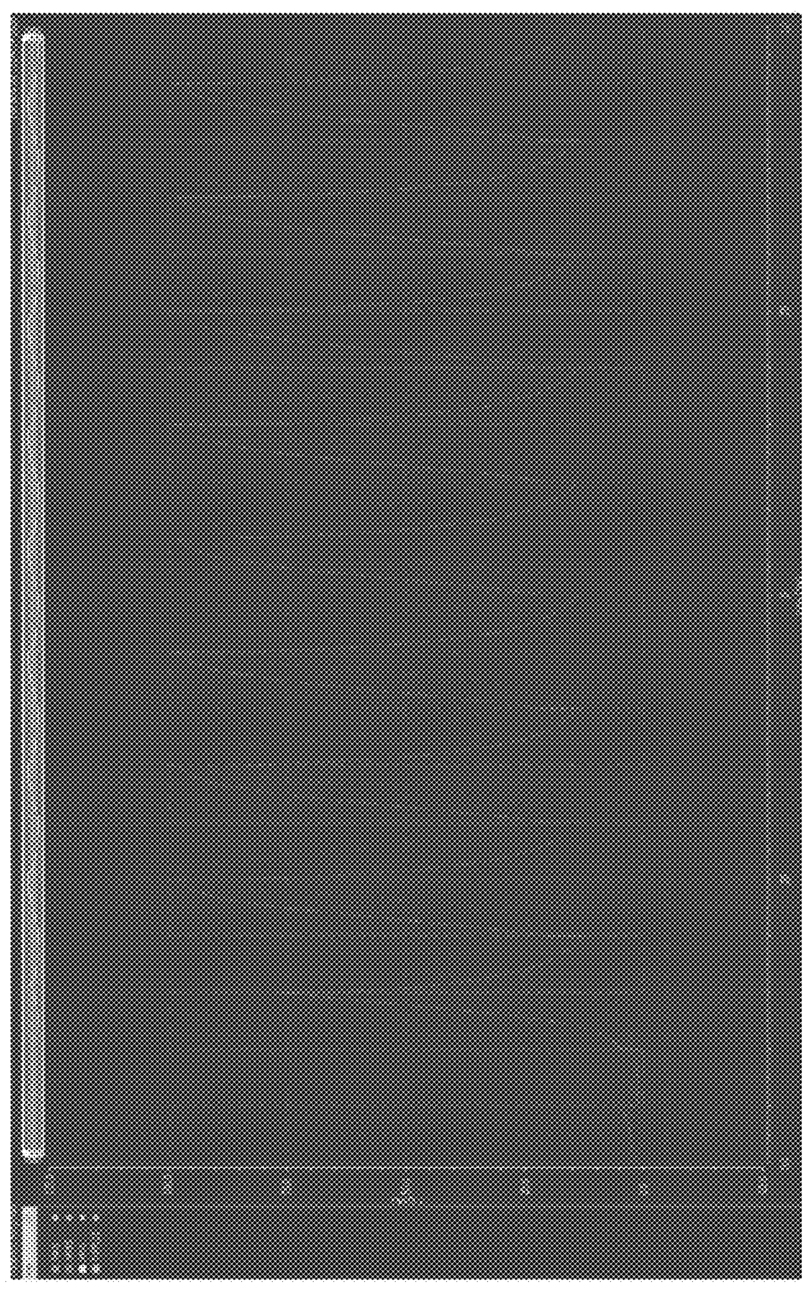
FIG. 14 is a circuit's solution for a triangle waveform input.

Equation 3 is the differential equation governing the solution of a Brownian particle inside a monostable well, with dx(t)/dt being the velocity of the particle and $s_{n,F}(t)$ being a band-pass filtered output signal. The analog integrated circuit may be implemented in a battery-operated system. In an embodiment, the analog integrated circuit may be implemented in a brain-computer interface applications. In another embodiment, the analog integrated circuit may be implemented in an implantable system. In yet another embodiment, the analog integrated circuit may be implemented in a wearable system. In any of these embodiments, the analog integrated circuit offers an energy-efficient means for weak signal detection, leading to long battery life. FIG. 13 is an embodiment of the analog integrated circuit, using TSMC 65 nm CMOS technology, with FIG. 14 being the circuit's solution of equation 1, for a triangle waveform input. In this embodiment, the circuit footprint is 100 square microns. However, other embodiments may accommodate footprints smaller and larger than 100 square microns. In this embodiment, the circuit is supplied by a 1 V single-supply and the total power consumption is less than 50 nanowatts. Other embodiments, however, may produce even lower power consumptions, based on the footprint of the circuit.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings.

The systems and methods disclosed herein may be implemented via one or more components, systems, servers, appliances, other subcomponents, or distributed between such elements. When implemented as a system, such systems may include and/or involve, inter alia, components such as software modules, general-purpose CPU, RAM, etc., found in general-purpose computers. In implementations where the innovations reside on a server, such a server may include or involve components such as CPU, RAM, etc., such as those found in general-purpose computers.

Additionally, the systems and methods herein may be achieved via implementations with disparate or entirely different software, hardware and/or firmware components, beyond that set forth above. With regard to such other components (e.g., software, processing components, etc.) and/or computer-readable media associated with or embodying the present implementations, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the systems and methods may be achieved via or performed by logic and/or logic instructions including program modules, executed in association with such components or circuitry, for example. In general, program modules may include routines, programs, objects, components, data structures, etc., that perform particular tasks or implement particular instructions herein. The embodiments may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, where media of any type herein does not include transitory media. Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the implementations described herein or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the implementations herein, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Additionally, the words "herein," "hereunder," "above," "below," and words of similar import refer to this application as a whole and not to any particular portions of this application.

Moreover, the above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A method for monitoring cellular activity in a tissue, the method comprising:

disposing the tissue within an extracellular medium;

contacting the tissue and extracellular medium with an electrode configured to detect signals generated by cellular activity within the tissue over time, wherein the cellular activity is measurable greater than 140 microns away from the electrode when pre-emphasizing spikes within the detected signals;

receiving the detected signals within a computer processor, wherein the detected signals have a first noise level, and wherein the processor is programmed to execute the processing steps of:

pre-emphasizing spikes within the detected signals by:

adding an additive noise to the detected signals;

filtering the detected signals with additive noise according to varying intensity via an algorithm based on stochastic resonance wherein a signal-to-noise ratio of spikes within the detected signals is enhanced by non-linear threshold detection based on Brownian particle movement in a monostable potential well;

generating an index array comprising indices of spikes within the detected signals having intensities exceeding one or more threshold;

grouping successive indices into a single value group to create a time array of detected spikes associated with cellular activity within the tissue; and generating an output identifying the time array of detected spikes.

2. The method of claim 1, wherein the tissue is at least one of neuronal tissue, cardiac tissue, lung tissue, muscle tissue, and bone tissue.

3. The method of claim 1, wherein the additive noise comprises at least one of white noise and flicker noise.

4. The method of claim 3, wherein the flicker noise has a variable frequency.

5. The method of claim 3, wherein a ratio of a standard deviation of the flicker noise and a standard deviation of the background noise is within a range of 0 and 75.

6. The method of claim 5, wherein the threshold is a multiple of the standard deviation of the background noise.

7. The method of claim 6, wherein the multiple of the standard deviation of background noise ranges between 3 and 5.

8. The method of claim 1, wherein the steps of adding, filtering, generating and grouping are executed with at least one of MATLAB, GNU Octave, and SciLAB.

9. The method of claim 1, wherein the signals are assessed for signal performance based on sensitivity.

10. The method of claim 1, wherein the one or more threshold comprises multiple thresholds.

11. The method of claim 1, wherein signals of similar amplitude are grouped together.

12. The method of claim 1, wherein signals of high activity are isolated from signals of silent to medium activity.

13. The method of claim 1, wherein values of the time array within 500 microseconds of the signal of closest proximity in the index array is considered as true positive.

14. The method of claim 1, wherein the Brownian particle movement in a monostable potential well is governed by the relationship $dx(t)/dt=-[ax(t)+bx^3(t)]+s_{n,F}(t)$, where $dx(t)/dt$ is a velocity of the particle at a position x within the well and $s_{n,F}(t)$ is a band-pass filtered output signal.

15. The method of claim 1, wherein the monostable potential well is underdamped.

16. A method for monitoring cellular activity in a tissue, the method comprising:

disposing the tissue within an extracellular medium;

contacting the tissue and extracellular medium with an electrode configured to detect signals generated by cellular activity within the tissue over time, wherein the cellular activity is measurable greater than 140 microns away from the electrode when pre-emphasizing spikes within the detected signals;

receiving the detected signals within a computer processor, wherein the detected signals have a first noise level;

using the processor, enhancing the detectability of spikes corresponding to cellular activity by pre-emphasizing spikes within the detected signals by:

adding an additive noise to the detected signals;

filtering the detected signals with additive noise according to varying intensity using stochastic resonance wherein a signal-to-noise ratio of spikes within the detected signals is enhanced by non-linear threshold detection;

generating an index array comprising indices of spikes within the detected signals having intensities exceeding one or more threshold;

grouping successive indices into a single value group to create a time array of detected spikes associated with cellular activity within the tissue; and generating an output identifying the time array of detected spikes.

17. The method of claim 16, wherein the tissue is at least one of neuronal tissue, cardiac tissue, lung tissue, muscle tissue, and bone tissue.

18. The method of claim 16, wherein the additive noise comprises at least one of white noise and flicker noise.

19. The method of claim 16, wherein the flicker noise has a variable frequency.

* * * * *